US007645299B2

(12) United States Patent
Koziol

(10) Patent No.: US 7,645,299 B2
(45) Date of Patent: Jan. 12, 2010

(54) INTRACORNEAL LENS SYSTEM HAVING CONNECTED LENSES

(76) Inventor: Jeffrey E. Koziol, 14 Ambrose, South Barrington, IL (US) 60610

( * ) Notice: Subject to any disclaimer, the term of this patent is extended or adjusted under 35 U.S.C. 154(b) by 605 days.

(21) Appl. No.: 10/878,525

(22) Filed: Jun. 29, 2004

(65) Prior Publication Data

US 2004/0243231 A1   Dec. 2, 2004

Related U.S. Application Data

(63) Continuation-in-part of application No. 10/608,545, filed on Jun. 30, 2003, now Pat. No. 7,008,447, which is a continuation of application No. 09/852,846, filed on May 11, 2001, now Pat. No. 6,589,280.

(51) Int. Cl.
    *A61F 2/14* (2006.01)
(52) U.S. Cl. .................. 623/5.12; 623/5.14; 623/6.34
(58) Field of Classification Search ....... 623/5.11–5.15, 623/6.34
    See application file for complete search history.

(56) References Cited

U.S. PATENT DOCUMENTS

| | | | |
|---|---|---|---|
| 4,477,158 A * | 10/1984 | Pollock et al. ............... 351/169 |
| 4,571,039 A * | 2/1986 | Poler ....................... 351/160 H |
| 4,624,669 A | 11/1986 | Grendahl |
| 4,704,016 A | 11/1987 | de Carle |
| 4,840,175 A | 6/1989 | Peyman |
| 4,906,245 A | 3/1990 | Grendahl |
| 5,024,517 A | 6/1991 | Seidner |
| 5,030,230 A | 7/1991 | White |
| 5,139,518 A | 8/1992 | White |
| 5,196,026 A | 3/1993 | Barrett et al. |
| 5,697,973 A * | 12/1997 | Peyman et al. ............. 623/6.26 |
| 5,722,971 A | 3/1998 | Peyman |
| 5,806,530 A | 9/1998 | Herrick |
| 5,876,439 A * | 3/1999 | Lee .......................... 623/5.12 |
| 5,919,185 A | 7/1999 | Peyman |
| 5,964,748 A | 10/1999 | Peyman |
| 6,015,435 A | 1/2000 | Valunin et al. |
| 6,059,775 A | 5/2000 | Nielsen |
| 6,063,073 A | 5/2000 | Peyman |
| 6,086,204 A | 7/2000 | Magnante |
| 6,090,141 A | 7/2000 | Lindstrom |
| 6,159,241 A * | 12/2000 | Lee et al. ................... 623/5.12 |
| 6,228,113 B1 | 5/2001 | Kaufman |
| 6,277,146 B1 | 8/2001 | Peyman et al. |
| 6,361,560 B1 * | 3/2002 | Nigam ..................... 623/5.14 |
| 6,543,453 B1 * | 4/2003 | Klima et al. ................ 128/898 |
| 6,589,280 B1 | 7/2003 | Koziol |
| 6,755,858 B1 * | 6/2004 | White ...................... 623/5.12 |

\* cited by examiner

*Primary Examiner*—David H Willse
*Assistant Examiner*—Javier G Blanco
(74) *Attorney, Agent, or Firm*—Roylance, Abrams, Berdo & Goodman, L.L.P.

(57) ABSTRACT

An in-phase intracorneal lens system that prevents substantial movement between connected lenses to provide high resolution of the eye. A first lens is adapted to be positioned on a surface of a cornea. A second lens has a substantially ring-shaped configuration and is substantially concentric with the first lens. At least one first bridge member extends from the first lens to the second lens to couple the first lens to the second lens to prevent substantial movement between the first and second lenses.

35 Claims, 5 Drawing Sheets

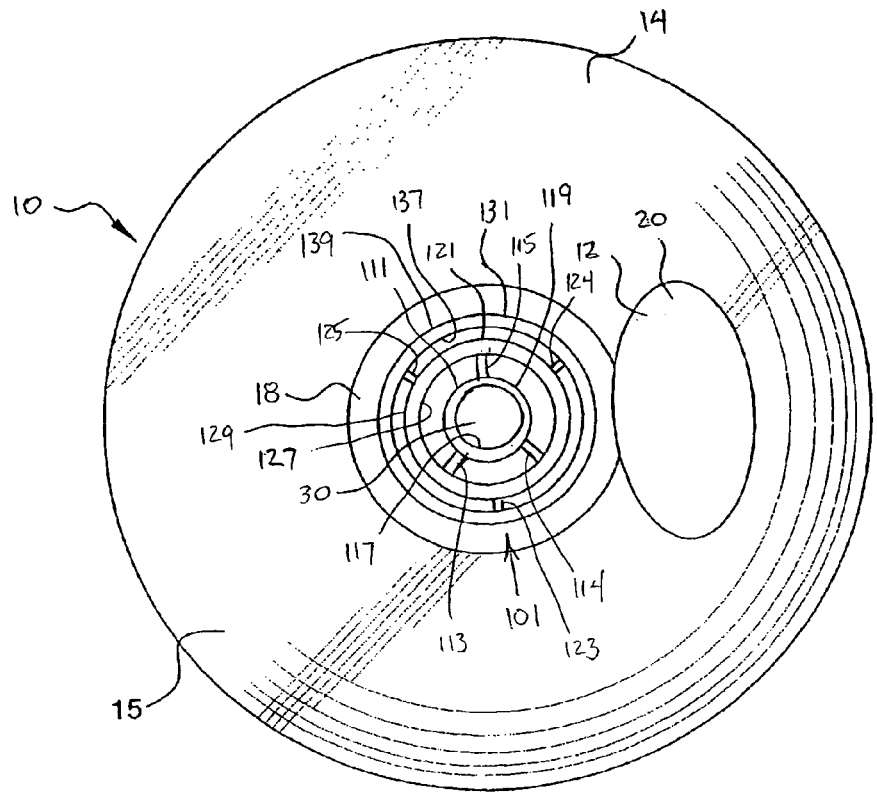
FIG. 16
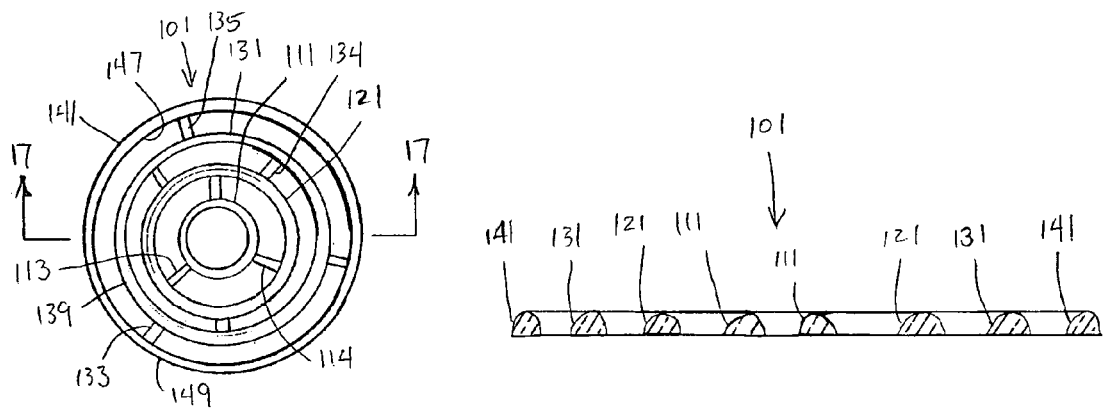
FIG. 17
FIG. 18

200~# INTRACORNEAL LENS SYSTEM HAVING CONNECTED LENSES

This application is a continuation-in-part of patent application Ser. No. 10/608,545, filed Jun. 30, 2003, which issued Mar. 7, 2006 as U.S. Pat. No. 7,008,447, which is a continuation of patent application Ser. No. 09/852,846, filed May 11, 2001, which issued Jul. 8, 2003 as U.S. Pat. No. 6,589,280, the entire contents of both of which are hereby incorporated by reference.

FIELD OF THE INVENTION

The present invention relates to a multifocal in-phase intracorneal lens system. More particularly, the present invention relates to at least two interconnected ring-shaped lenses in which substantial movement of the lenses with respect to another when implanted in a live cornea is prevented. Still more particularly, the present invention relates to implanting at least two interconnected lenses in a live cornea to increase the diffusion of nutrients through the cornea, while increasing the resolution of the eye.

BACKGROUND OF THE INVENTION

Conventional surgical techniques use ultraviolet light and short wavelength lasers to modify the shape of the cornea. For example, excimer lasers, such as those described in U.S. Pat. No. 4,840,175 to Peyman, which is incorporated herein by reference, emit pulsed ultraviolet radiation, which can be used to decompose or photoablate tissue in the live cornea to reshape the cornea.

Specifically, the Peyman patent discloses the laser surgical technique known as laser in situ keratomycosis (LASIK). In this technique, a portion of the front of the live cornea can be cut away in the form of a flap having a thickness of about 160 microns. This cut portion is moved away from the live cornea to expose an inner surface of the cornea. A laser beam is then directed onto the exposed inner surface to ablate a desired amount of the inner surface up to 150-180 microns deep. The cut portion is reattached over the ablated portion of the cornea and assumes a shape conforming to that of the ablated portion. The LASIK procedure is generally sufficient to correct myopia or distance vision. However, in many patients while the LASIK procedure is sufficient to correct distance vision it does not correct reading vision in patients who are presbyopic. Presbyopia is a condition which occurs after age 40 in which the lens of the eye loses its ability to change focus. When a distinctive object is in sharp focus on the retina, close objects are out of focus or blurred. To bring close objects into focus the lens of the eye changes shape to bring these objects into focus. This rapid movement of the lens occurs without conscience thought through and allows objects to be brought into focus. When the lens of the eye losses this ability, reading glasses or bifocal glasses are used. When a patient in their 40's and 50's have laser surgery and achieve corrected distance vision they still need glasses for reading. There are frequently 2 pairs needed one for intermediate distance, such as the computer and one for close reading vision.

Additional methods for correcting the refractive error in the eye include inserting an implant in between layers of the cornea. Generally, this is achieved using several different methods. The first method involves inserting a ring between layers of the cornea, as described in U.S. Pat. No. 5,405,384 to Silvestrini. Typically, a dissector is inserted in to the cornea to form a channel therein. Once the dissector is removed, a ring is then inserted into the channel to alter the curvature of the cornea. In the second method, a flap can be created similarly to the LASIK procedure, described above, and a large lens can be inserted under the flap to change the shape of the cornea, as described in U.S. Pat. No. 5,919,785 to Peyman and U.S. Pat. No. 6,102,946 to Nigam. The third method involves forming a pocket using a mechanical instrument, and inserting an implant into the pocket, as described in U.S. Pat. No. 4,655,774 to Choyce. These procedures all induce a single corneal curvature change and do not correct both distance vision and close vision in a bifocal or multifocal manner.

Additionally, even though these existing intracorneal lenses are somewhat suitable for correcting distant vision disorders, they typically cause the eye to experience an undesirable side effect commonly referred to as a "halo effect", which is a ring of light that a person will see in the eye having an implanted intracorneal lens. A halo effect is caused due to light entering into or being refracted by the intracorneal lens at certain angles which creates a glare that is sensed by the retina of the eye and thus experienced by the person.

Although the severity of the halo effect can vary depending on the shape of the intracorneal lens and the amount of direct and ambient light being received by the eye, the halo effect can cause the patient much annoyance. Also, in certain instances, the halo effect can also adversely affect the patient's ability to read, drive a car and perform other routine activities requiring acute vision.

Additionally, many of these conventional techniques require relatively large lenses or corneal implants that stretch or expand the corneal surface to accommodate the intracorneal lens. These large lenses can lead to corneal erosion, which is generally caused by corneal cells dying since the lens does not allow nutrients to flow through portions of the cornea.

Accordingly, a need exists for intracorneal lenses, which can help correct the vision in the eye without displacing the corneal surface, while simultaneously eliminating or reducing glare and the halo effect due to light reflecting off of the intracorneal lens.

Multiple intracorneal lenses can be implanted in a live cornea to correct various problems with an eye, as shown in my U.S. Pat. No. 6,589,280. However, movement of one lens with respect to another lens results in decreased resolution of the eye. A need exists for preventing substantial movement of one lens with respect to another lens after implanting multiple lenses in a live cornea.

Intracorneal lenses are often perforated to increase the diffusion of nutrients through the cornea. However, perforations in an implanted intracorneal lens results in decreased resolution of the eye. A need exists for intracorneal lenses that allow for diffusion of nutrients through the eye, without resulting in decreased resolution.

A need exists for improved intracorneal lenses.

SUMMARY OF THE INVENTION

Accordingly, it is an object of the present invention is to provide an improved method for correcting the vision of an eye.

Another object of the present invention is to provide a method for correcting the vision of an eye by inserting or implanting an intracorneal lens.

Still another object of the present invention is to provide a method for correcting the vision of an eye by inserting an intracorneal lens, without the lens substantially altering the shape of the cornea, so that undue tension is not experienced by the corneal flap.

Yet another object of the present invention is to provide a method for correcting the vision of an eye by inserting an intracorneal lens that changes the refraction of the eye by having a different refractive index than the corneal tissue.

Yet another object of the present invention is to provide a method for correcting the vision of an eye using multiple microscopic lenses, so that glare can be reduced or eliminated.

Yet another object of the present invention is to provide a method for correcting the vision of an eye by placing multiple microscopic lenses under a corneal flap.

Yet another object of the present invention is to provide a method for correcting the distance vision and close vision of an eye.

Still another object of the present invention is to provide a method of increasing the resolution of an eye.

Still another object of the present invention is to provide at least two connected lenses that are adapted to be implanted in the eye to increase resolution.

Still another object of the present invention is to provide at least two connected intracorneal lenses that are prevented from substantially moving with respect to one another.

Still another object of the present invention is to provide a method of increasing the resolution of the eye while allowing nutrient diffusion through the cornea.

The foregoing objects are basically attained by an intracorneal lens system, including a first lens adapted to be positioned on a surface of a cornea; a second lens having a substantially ring-shaped configuration and being substantially concentric with the first lens; and at least one first bridge member extending from the first lens to the second lens to couple the first lens to the second lens to prevent substantial movement between the first and second lenses.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure:

FIG. 16 is a front elevational view of an eye in which at least two connected ring-shaped lenses have been implanted in a live cornea.

FIG. 17 is a front elevational view of four substantially ring-shaped lenses connected by bridges.

FIG. 18 is a cross-sectional side view taken along lines 17-17 of FIG. 16.

DETAILED DESCRIPTION OF THE PREFERRED EMBODIMENT

Figure 1:
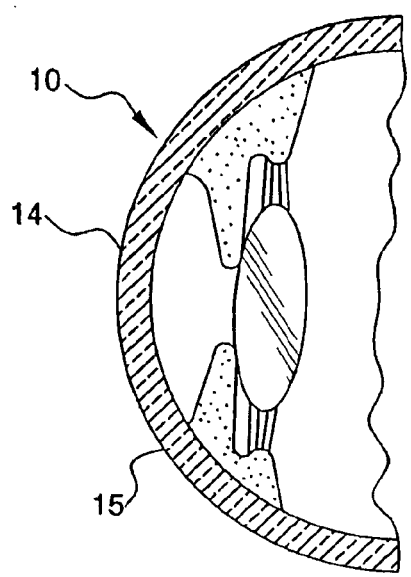
FIG. 1 is a cross-sectional side view of an eye.

As seen in FIGS. 1-7, the refractive properties of eye 10 can be altered by creating a corneal flap 12 in the cornea 14, ablating the cornea to reshape the cornea and the external surface 15 of the cornea, and then placing multiple microscopic lenses or inlays 16 under flap 12.

To begin, the refractive error in the eye is measured using wavefront technology, or any other measurement device desired, as is known to one of ordinary skill in the art. For a more complete description of wavefront technology see U.S. Pat. No. 6,086,204 to Magnate, the entire contents of which is incorporated herein by reference. The refractive error measurements are then used to determine the proper correction necessary. For example, the information from the wavefront technology determines the proper portions of the cornea of the eye to be ablated, if necessary, and the proper power of the lenses 16 and/or the number of the lenses 16 to be implanted.

Figure 2:
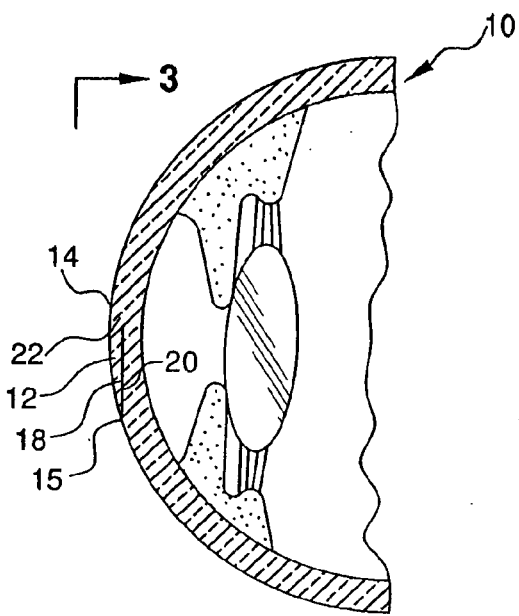
FIG. 2 is a cross-sectional side view of the eye of FIG. 1 with a flap formed thereon.
Figure 3:
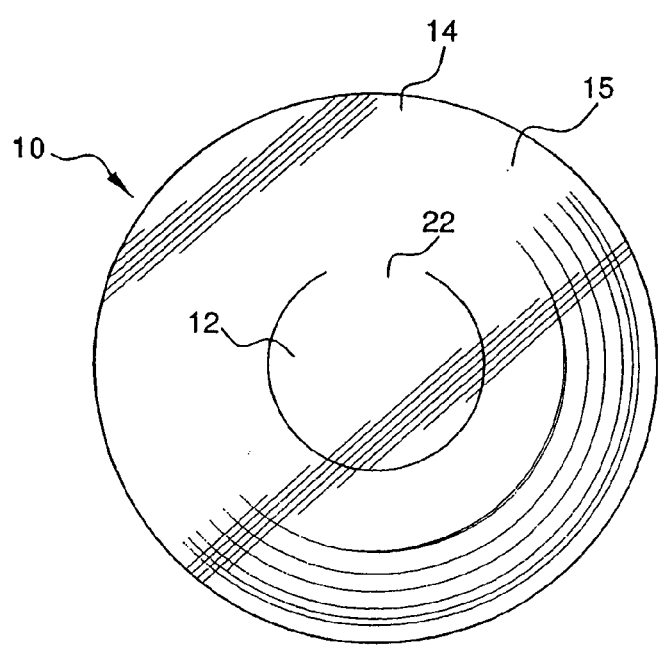
FIG. 3 is a front elevational view taken along lines 3-3 of FIG. 2.

As seen in FIGS. 2 and 3, flap 12 is created on the surface of the cornea by using a tool or device (not shown) that is known to one skilled in the art, such as a microkeratome. The device separates the cornea and exposes a first surface 18 and a second surface 20. The first surface 18 faces in an anterior direction and the second surface 20 faces in a posterior direction of the eye. The flap is moved to expose second surface 20 using a spatula, forceps or any other device desired. The flap 12 is preferably coupled or connected to the cornea by a portion 22 that allows the flap to be moved away from or peeled from surface 18 in a hinged manner, as seen specifically in FIGS. 4-6 and 8. However, the flap does not necessarily need to be coupled to the cornea in a hinged manner and can be fully removed from the cornea or a pocket can be formed underneath the external surface of the cornea, with an incision allowing access to the pocket.

Figure 4:
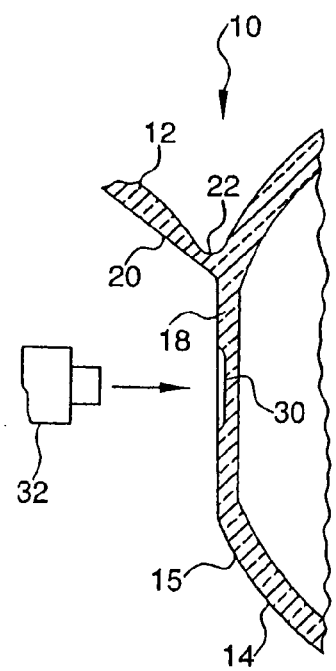
FIG. 4 is a cross-sectional side view of the eye in FIG. 3 with the flap moved away from the surface of the cornea and a laser ablating an exposed surface of the cornea.

If the refractive error of the cornea requires correcting for distance vision, such as myopia, the LASIK procedure or any other technique known in the art can be preformed. Preferably, LASIK, as disclosed in U.S. Pat. No. 4,840,175 to Peyman and is known to one of ordinary skill in the art, is used and preferably a portion 30 of surface 18 and surface 20 of the cornea under corneal flap 12 is ablated using an excimer laser 32 to achieve the proper corrective vision for distances, as seen in FIG. 4. However, a portion of surface 20 can be ablated or a portion of both surfaces 18 and 20 can be ablated. If no distance vision correction is required, it is not necessary to perform the LASIK procedure or any other distance corrective procedure known in the art.

Figure 5:
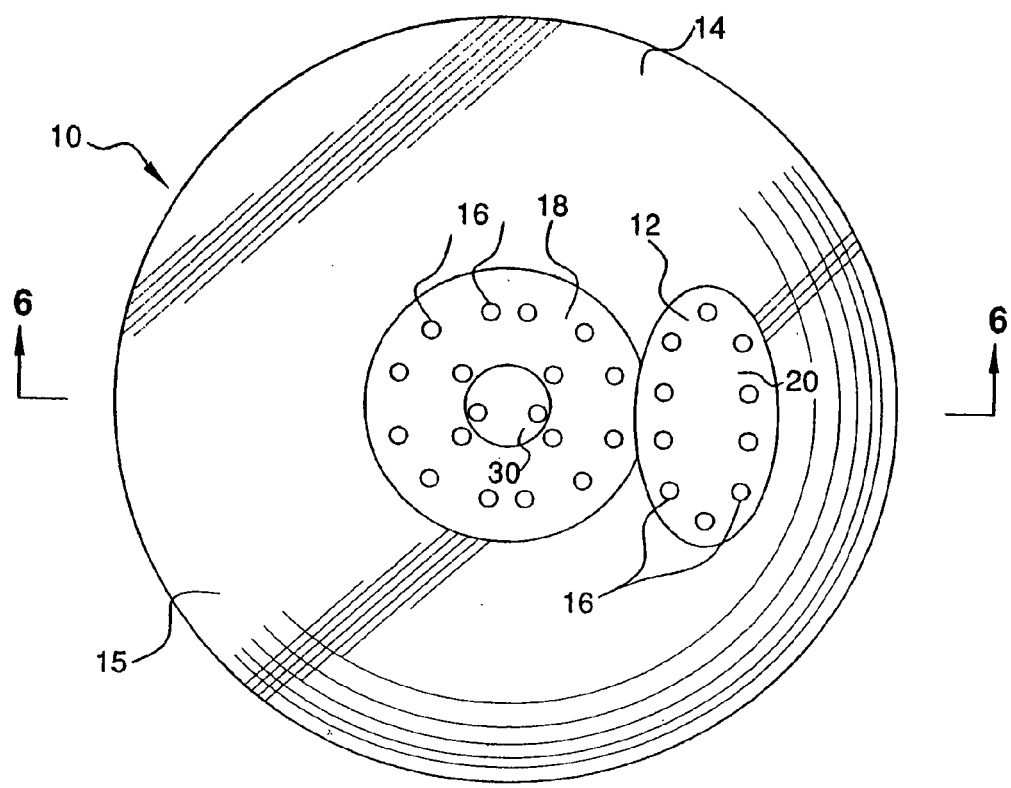
FIG. 5 is a front elevational view of an eye undergoing a preferred method of the present invention, specifically, microscopic lenses are placed on both the first and second exposed internal corneal surfaces.
Figure 6:
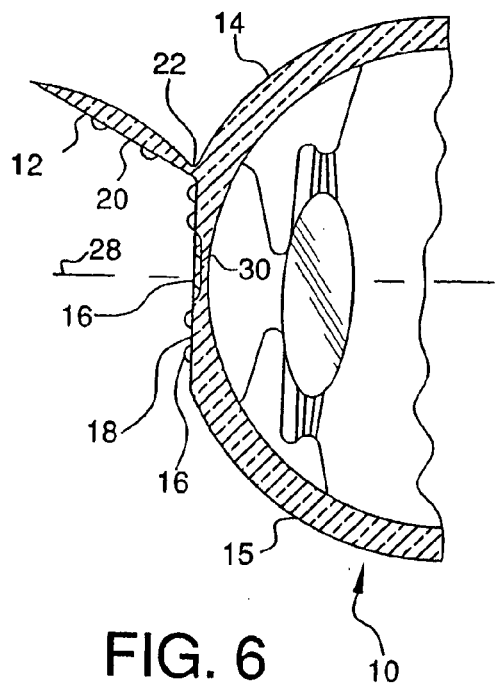
FIG. 6 is a cross-sectional side view taken along lines 6-6 of FIG. 5.
Figure 8:
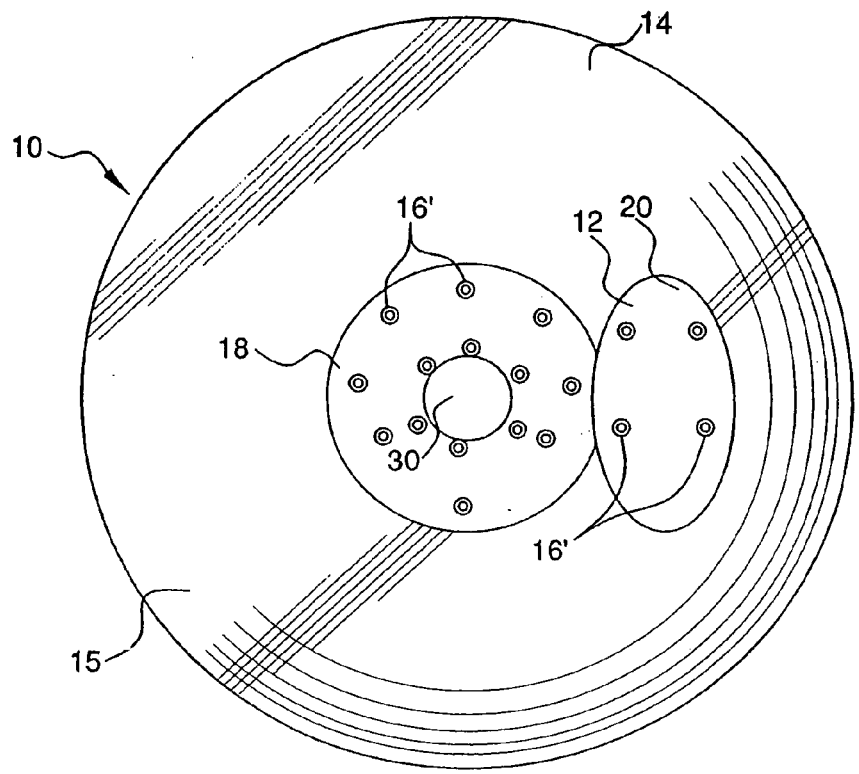
FIG. 8 is a front elevational view of an eye undergoing the preferred method of the present invention, wherein the microscopic lenses are substantially ring-shaped.
Figures 9, 10:
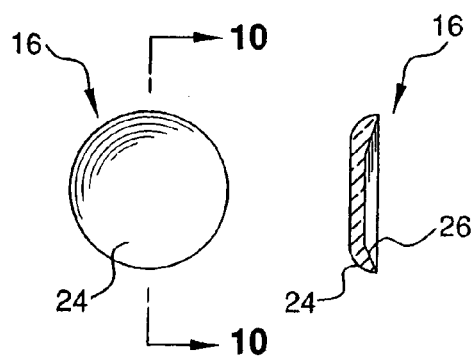
FIG. 9 is a front elevational view of a microscopic lens used in the method described herein.
FIG. 10 is a cross-sectional side view taken along lines 10-10 of FIG. 9.
Figures 11, 12:
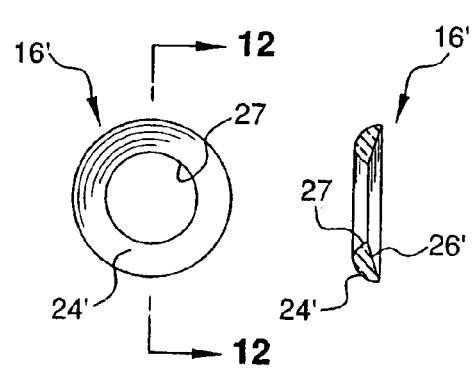
FIG. 11 is a front elevational view of a substantially ring-shaped microscopic lens used in the method described herein.
FIG. 12 is a cross-sectional side view taken along lines 12-12 of FIG. 11.

To correct for reading or to allow the eye to focus on close objects, either after a distance corrective procedure or simply after the flap is formed, if no distance correction is necessary, microscopic lenses 16 and 16' are inserted under flap 12, as seen in FIGS. 5, 6 and 8. Each lens 16 and 16' has a first surface 24 or 24' and a second surface 26 or 26', respectively. The lenses are preferably substantially circular with an arcuate cross section, as seen in FIGS. 9 and 10, and lens 16' is substantially ring shaped with an arcuate cross section, as seen in FIGS. 8, 11 and 12. Ring shaped lenses 16' have a hole or an aperture, therethrough defined by an inner wall or surface 27. The lenses 16 and 16' are preferably "microscopic" in size. "Microscopic", in this instance means that the size of each lens 16 and 16' is preferably about one millimeter in diameter and about 1-50 microns thick, and more preferably, each lens 16 and 16' is less than about one millimeter in diameter and about 2-3 microns thick. This "microscopic" size allows nutrients to easily flow through the lens and therefore eliminates or at least reduces corneal erosion. It is noted, however, that the lenses 16 may be any shape desired or be diffractive or holographic elements. For example, each lens 16 may be substantially flat or planar, with surfaces 24 and 26 being substantially parallel with each other. Each lens preferably has a power of between about plus one to about plus three diopters. However, the power of each lens may be any power desired, but preferably at least different from that of the refractive power of the cornea.

Figure 13:
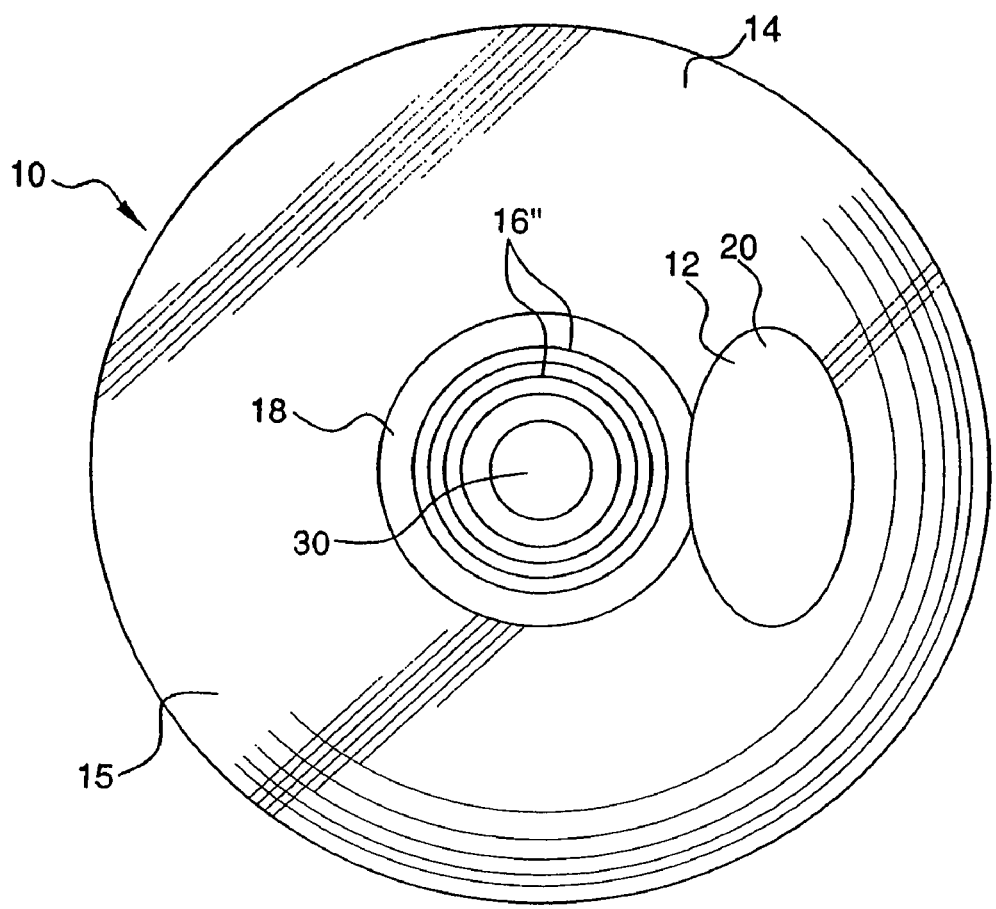
FIG. 13 is a front elevational view of an eye undergoing the preferred method of the present invention, wherein there is one substantially ring-shaped lens having a microscopic ring portion.
Figure 14:
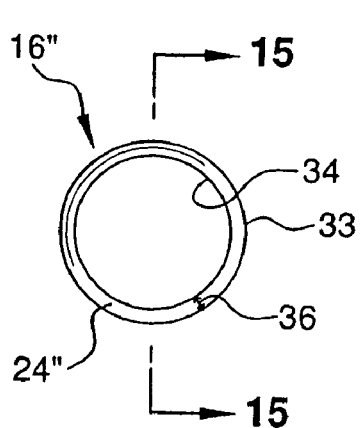
FIG. 14 is a front elevational view of a substantially ring-shaped lens having a microscopic ring portion used in the method described herein.
Figure 15:
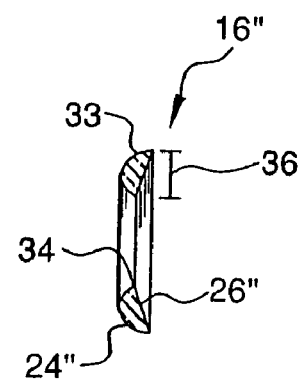
FIG. 15 is a cross-sectional side view taken along lines 15-15 of FIG. 14.

Furthermore, as shown in FIG. 13, microscopic lens 16" can be a substantially ring shaped lens with an arcuate cross section and first and second surfaces 24" and 26", as seen in FIGS. 14 and 15. Lens 16" has an outside wall or surface 32 and inside wall or surface 34 that have diameters that are sufficiently large enough to encircle the main optical axis of the eye 28 with the center of the ring, aligned with the main optical axis. In other words, the diameter of wall 32 is preferably about 3-5 millimeters, but can be any size desired. However, the distance or ring portion 36 between wall 32 and wall 34 and the thickness of lens 16" is preferably microscopic. As described above, microscopic as defined herein means preferably that distance 36 is about one millimeter and the thickness of lens 16" is about 1-50 microns thick, and more preferably, distance 36 is less than about one millimeter and lens 16" is about 2-3 microns thick. Preferably, multiple rings 16" are placed under the flap, as shown in FIG. 13. The lenses are placed or positioned in concentric circles of about 3, 4 and/or 5 millimeters around the main optical axis, each having a different refractive power, thus allowing multifocal vision. However, any number of lenses can be placed around the main optical axis and, including only one or any number greater than one, and the lenses may each have the same refractive power or any combination of the same or different refractive power. In other words, two lenses can have the same refractive power and one lens can have a different refractive power.

Lenses 16, 16' and 16" are preferably formed of any polymer or synthetic material desired, such as plastic, glass, silicon, methametacolade, or any acrylic that preferably has a refractive index that is different from the refractive index of the cornea. However, the lenses may be any material desired that would help correct the refractive error in the cornea.

Preferably, second surface 26 of at least one microscopic lens 16 is placed on the first corneal surface 18 of cornea 14. However, first surface 24 may be placed on second corneal surface 20 or any combination thereof when multiple lenses are used. For example, first surface 24 of at least one lens can be placed on corneal surface 20, while second surface 26 of at least one lens can be placed on corneal surface 18.

More preferably, when lenses 16 and 16' are used, about 50 microscopic lenses are placed in between the first and second surfaces 18 and 20; however, any number of lenses desired to correct the refractive error in the cornea can be placed in between the first and second surfaces 18 and 20. Depending on the power of the lenses, by inserting the lenses in this manner an eye will be able to see with either bifocal or multifocal vision. For example, about 50 lenses, each having the same power can be placed in concentric circles about the main optical axis 28 of the eye. This pattern would allow the patient to view distance vision using the portion of the eye that has no microscopic lenses, while the portions that had microscopic lenses would allow a patient to view objects close, such as for the purpose of reading. Additionally, different power lenses can be implanted that would allow multifocal vision. For example, one array of about 20 plus 1.5 diopter lenses can be placed in the eye in any manner desired (i.e. a concentric circle), while a second array of about 20 plus 2 diopter lenses can also be placed in the eye in any manner desired (i.e. a concentric circle). Furthermore, when using lens 16", multiple lenses can be used in concentric circles, each lens having either the same refractive index as each other lens, or a different refractive index or any combination thereof that would allow bifocal or multifocal vision as described above. This allows several different focusing points for the eye, allowing the patient to see a variety of near and far distances.

Figure 7:
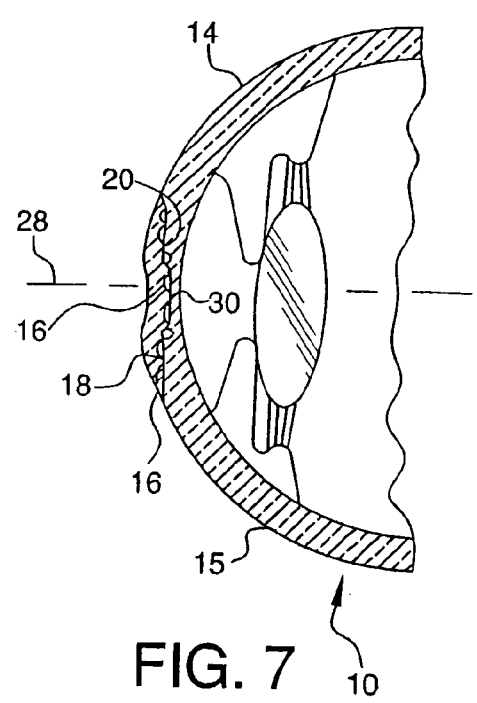
FIG. 7 is a cross-sectional side view of the eye of FIG. 6 with the flap replaced over the exposed surface of the cornea and the microscopic lenses.

As seen in FIG. 7, once the lens or lenses are in place, the flap is replaced or repositioned on the cornea. Preferably, surface 20 is placed back over surface 18, in the same position prior to removing flap 12. The flap is then sutured or reattached to the cornea in any manner desired or simply replaced and allowed to heal.

Since each of the lenses 16 are preferably less than about 2-3 microns thick, the first corneal surface 18 is not substantially displaced away from second corneal surface 20. In other words, the exterior surface of the cornea has approximately the same curvature as the eye originally has or has after the distance correcting procedure. This allows little or no tension to be exerted over the flap 12 when it is reattached and allows for a relatively precise fit of surface 18 and surface 20.

Additionally, the lenses 16 allow for bifocal and multifocal vision by focusing the light passing therethrough on a different portion of the retina, since the refractive power of each lens is different from the refractive power of the cornea. Therefore, once it is known what refractive error is in the cornea and the eye, the only values to be determined are whether distance correction is necessary, the power of the lenses, or the powers of the lenses for multifocal purposes, and the number of lenses.

The implantation of microscopic lenses 16 allow vision correction, while being small enough so as to not produce significant glare refracted from the lenses or substantially displace the surface of the cornea or the flap 12. This procedure improves vision without discomforting glare problems or the undue stress on the cornea experienced by the prior art.

Any discussion of lens 16 and sides 24 and 26 applies to lenses 16' and 16" and to sides 24', 24", 26' and 26".

An in-phase intracorneal lens system 101 is shown in FIGS. 16-18. A first ring-shaped lens 111 is adapted to be positioned on a surface 18 of a cornea 14. A second lens 121 has a substantially ring-shaped configuration and substantially surrounds and is substantially concentric with the first lens 111, as shown in FIGS. 16-18. At least one substantially straigh first bridge member 113 extends substantially radially from the first lens 111 to the second lens 121 to couple the first lens to the second lens to prevent substantial movement between the first and second lenses, which increases the resolution of the eye. The interconnected lenses provide substantially the same resolution as a single lens of the same area, with the additional benefit of having open areas to facilitate diffusion of nutrients through the cornea. Preferably, the bottoms of the interconnected lenses, as shown in FIGS. 16-18, are substantially planar and located in the same first plane. The tops of these lenses are preferably located in a second plane that is substantially parallel to the first plane.

The first lens 111 is preferably positioned substantially concentrically with the main optical axis of the eye. The second lens 121 has an inner diameter 127 that is spaced from the outer diameter 117 of the first lens, as shown in FIGS. 16-18. At least one first bridge member 113 connects the first and second lenses. Preferably, three equidistantly circumferentially spaced and substantially radially oriented first bridge members 113, 114 and 115 connect the first and second lenses, these bridge-members being substantially straight, as are the other bridge-members discussed hereinafter. Providing space between the first and second lenses 111 and 121 facilitates diffusion of nutrients through the cornea 14 since the nutrients do not have to pass through a lens in that space. In one embodiment, one of the first or second lenses is a minus lens and the other lens is a plus lens.

A third lens 131 having a substantially ring-shaped configuration may be positioned substantially concentrically with the second lens 121, as shown in FIGS. 16-18. The third lens 131 has an inner diameter 137 that is spaced from an outer diameter 129 of the second lens 121. At least one second bridge member 123 connects the second and third lenses 121 and 131. Preferably, three equidistantly circumferentially spaced and substantially radially oriented second bridge members 123, 124 and 125 connect the second and third lenses 121 and 131.

A fourth lens 141 having a substantially ring-shaped configuration may be positioned substantially concentrically with the third lens 131, as shown in FIGS. 16-18. The fourth lens 141 has an inner diameter 147 that is spaced from an outer diameter 139 of the third lens 131. At least one third bridge member 133 connects the third and fourth lenses 131 and 141. Preferably, three equidistantly circumferentially spaced and substantially radially oriented third bridge members 133, 134 and 135 connect the third and fourth lenses 131 and 141.

Any number of additional lenses may be added to the system, but preferably the in-phase intracorneal lens system 101 has between two and four lenses. One limitation on the number of lenses usable with the in-phase intracorneal lens system 101 is that additional lenses lose their effectiveness once they have passed beyond the main optical axis or zone of the eye.

As discussed above, flap 12 is created on the surface of the cornea 14 by using a tool or device (not shown) that is known to one skilled in the art, such as a microkeratome. The device separates the cornea 14 and exposes a first surface 18 and a second surface 20. The first surface 18 faces in an anterior direction and the second surface 20 faces in a posterior direction of the eye. The flap is moved to expose second surface 20 using a spatula, forceps or any other device desired. The flap 12 is preferably coupled or connected to the cornea by a portion 22 that allows the flap to be moved away from or peeled from surface 18 in a hinged manner, as shown in FIG. 16. However, the flap 12 does not necessarily need to be coupled to the cornea in a hinged manner and may be fully removed from the cornea or a pocket may be formed underneath the external surface of the cornea, with an incision allowing access to the pocket.

To correct vision problems of an eye, the in-phase intracorneal lens system 101 according to the present invention, is inserted under flap 12, as seen in FIG. 16. Each lens is substantially ring-shaped with an arcuate cross section, as shown in FIGS. 16-18. Ring-shaped lenses 111, 121, 131 and 141 have inner diameters 117, 127, 137 and 147, respectively, and outer diameters 119, 129, 139 and 149, respectively. The lenses may be tinted or polarized to eliminate glare.

The bridge members connect the outer diameter of one lens with the inner diameter of the next outer lens. Each lens preferably has a refractive power of between about plus one to about plus three diopters. However, the power of each lens may be any power desired, but preferably at least different from that of the refractive power of the cornea. To ensure high resolution of the eye, each of the lenses has approximately the same power. The bridge members are preferably transparent and prevent substantial movement between lenses, thereby creating a lens system 101 providing an eye with high resolution.

Multiple intracorneal lenses only provide high resolution when all the lenses are in-phase. To be in-phase, each wavelength of light hitting the lenses hits the surface of each lens at the same point of wave oscillation of the light. When multiple intracorneal lenses are implanted in a cornea, movement between the lenses prevents the lenses from staying in-phase, thereby lessening the resolution of the eye. The bridge members of the present invention prevent substantial movement of the implanted lenses, thereby increasing the resolution of the eye provided by the intracorneal lens system 101

Preferably, there is about a 0.25 to 0.50 mm gap between successive outer and inner diameters of the lenses in the system 101. Each of the lenses 111, 121, 131 and 141 preferably has a radial width of 0.25 to 0.50 mm, with an outer diameter preferably ranging from about 2 mm to about 5 mm. Preferably, the thickness of a lens is about 0.005 to about 0.250 mm, i.e., the distance from the bottom edge to the top edge of the lens. The lenses and the bridge members of the intracorneal lens system 101 are preferably integrally formed as one piece of material. Any suitable material may be used to make the lenses and bridge members, but preferably polycarbonate or a methyl methacrylate material is used. The lenses of the system are easily foldable to facilitate easy insertion through the small incision made in the cornea 14.

The intracorneal lens system 101 of the present invention may also be implanted in conjunction with an intraocular lens system (IOL) to provide a multifocal or bifocal system.

As generally shown in FIG. 7, once the in-phase intracorneal lens system is in place, the flap is replaced or repositioned on the cornea. Preferably, surface 20 is placed back over surface 18, in the same position prior to removing flap 12. The flap is then sutured or reattached to the cornea in any manner desired or simply replaced and allowed to heal.

While preferred embodiments have been chosen to illustrate the invention, it will be understood by those skilled in the art that various changes and modifications may be made therein without departing from the scope of the invention as defined in the appended claims.

What is claimed is:

1. An intracorneal lens system, comprising:
a first innermost intracorneal lens adapted to be positioned on a surface beneath an outer surface of a cornea, said first lens being ring-shaped with no lens being disposed within an inner diameter of said first lens;

a second intracorneal lens having a substantially ring-shaped configuration and being substantially concentric with said first lens; and at least one first bridge member extending from an outer diameter of said first lens to an inner diameter of said second lens and coupling said first lens to said second lens to prevent substantial movement between said first and second lenses, wherein said first and second lenses and said at least one first bridge member are substantially coplanar, said first and second lenses are concentric, and said first and second lenses and said first bridge member are integrally formed as one piece of material, wherein said at least one first bridge member includes at least three first bridge members, wherein said at least three first bridge members are spaced substantially equidistantly from each other, and wherein an outer diameter of said first lens is spaced from an inner diameter of said second lens.

2. A lens system according to claim 1, wherein said first lens is adapted to be positioned substantially concentrically with a main optical axis of the eye.

3. A lens system according to claim 1, wherein
said first lens is a minus lens and said second lens is a plus lens.

4. A lens system according to claim 1, wherein
said first lens is a plus lens and said second lens is a minus lens.

5. A lens system according to claim 1, wherein
a third lens having a substantially ring shaped configuration is positioned substantially concentrically with said second lens.

6. A lens system according to claim 5, wherein
at least one second bridge member couples said third lens to said second lens.

7. A lens system according to claim 6, wherein
said at least one second bridge member includes at least three second bridge members.

8. A lens system according to claim 7, wherein
said at least three second bridge members are spaced substantially equidistantly from each other.

9. A lens system according to claim 6, wherein
an inner diameter of said third lens is spaced from an outer diameter of said second lens.

10. A lens system according to claim 5, wherein
a fourth lens having a substantially ring shaped configuration is positioned substantially concentrically with said third lens.

11. A lens system according to claim 10, wherein
at least one third bridge member couples said fourth lens to said third lens.

12. A lens system according to claim 11, wherein
said at least one third bridge member includes at least three third bridge members.

13. A lens system according to claim 12, wherein
said at least three third bridge members are spaced substantially equidistantly from each other.

14. A lens system according to claim 11, wherein
an inner diameter of said fourth lens is spaced from an outer diameter of said third lens.

15. A lens system according to claim 1, wherein said first and second lenses and said first bridge member are made of a polycarbonate or a methyl methacrylate material.

16. A lens system according to claim 1, wherein
said first and second lenses are tinted or polarized to substantially eliminate glare.

17. An intracorneal lens system for implantation in an eye, comprising:

a first innermost intracorneal lens having an opening therein and a first inner diameter and a first outer diameter, said first lens adapted to be positioned beneath an outer surface of a cornea in the eye and concentric with a main optical axis of the eye, said first lens being ring-shaped with no lens being disposed within said opening of said first lens;

a second intracorneal lens having a second inner diameter and positioned outside of said first outer diameter of said first lens, said second lens being substantially ring-shaped; and a first coupling member extending from said first outer diameter to said second inner diameter and coupling said first lens to said second lens, wherein said first and second lenses and said first coupling member are substantially coplanar, said first and second lenses are concentric, and said first and second lenses and said first coupling member are integrally formed as one piece of material, and at least two additional first coupling members extending from said first outer diameter to said second inner diameter to couple said first lens to said second lens, wherein said first coupling members are spaced substantially equidistantly from each other, and wherein said first lens is spaced from said second lens.

18. A lens system according to claim 17, wherein
said first lens has a first refractive power; and
said second lens has a second refractive power, said second refractive power being substantially different than said first refractive power.

19. A lens system according to claim 17, wherein
said first lens is a minus lens and said second lens is a plus lens.

20. A lens system according to claim 17, wherein
said first lens is a plus lens and said second lens is a minus lens.

21. A lens system according to claim 17, further including
a third lens having a substantially ring shaped configuration and being substantially concentric with said second lens.

22. A lens system according to claim 21, wherein
a second coupling member couples said third lens to said second lens.

23. A lens system according to claim 22, wherein
said second lens is spaced from said first lens, and said third lens is spaced from said second lens.

24. A lens system according to claim 22, wherein
a fourth lens having a substantially ring shaped configuration is positioned substantially concentrically with said third lens.

25. A lens system according to claim 24, wherein
at least one third coupling member couples said fourth lens to said third lens.

26. A lens system according to claim 25, wherein
said at least one third coupling member includes at least three third coupling members.

27. A lens system according to claim 26, wherein
said at least three third coupling members are spaced substantially equidistantly from each other.

28. A lens system according to claim 25, wherein
said first, second, third and fourth lenses and said first, second and third coupling members are integrally formed.

29. A lens system according to claim 28, wherein
said first, second, third and fourth lenses and said first, second and third bridge members are made of a polycarbonate or a methyl methacrylate material.
30. A lens system according to claim 25, wherein
said first, second, third and fourth lenses have substantially the same power.
31. A lens system according to claim 25, wherein
said first, second, third and fourth lenses are tinted or polarized to substantially eliminate glare.
32. A lens system according to claim 24, wherein
an inner diameter of said fourth lens is spaced from an outer diameter of said third lens.
33. A lens system according to claim 17, wherein
said first and second lenses have first and second lower surfaces that are substantially planar and are located in a first plane.
34. A lens system according to claim 33, wherein
said first and second lenses have first and second upper surface that are substantially planar and are located in a second plane.
35. A lens system according to claim 34, wherein
said first and second planes are substantially parallel.

\* \* \* \* \*